United States Patent [19]

Jouquey et al.

[11] Patent Number: 4,664,850

[45] Date of Patent: May 12, 1987

[54] NOVEL RADIOACTIVE STEROIDS

[75] Inventors: Alain Jouquey, Paris; Daniel Philibert, La Varenne Saint Hilaire; Martine Moguilewsky, Nogent sur Marne; Jean-Noël Veltz, Saint-Denis, all of France

[73] Assignee: Roussel Uclaf, Paris, France

[21] Appl. No.: 620,457

[22] Filed: Jun. 14, 1984

[30] Foreign Application Priority Data

Jun. 14, 1983 [FR] France .................. 83 09811

[51] Int. Cl.$^4$ ............................................. C07J 1/00
[52] U.S. Cl. ........................... 260/397.45; 260/397.5
[58] Field of Search .................................. 260/397.45

[56] References Cited

U.S. PATENT DOCUMENTS 4,233,297 11/1980 Teutsch .................... 260/397.45

OTHER PUBLICATIONS

Steroids, vol. 31, (1978), No. 1, an article by Evans et al., pp. 69–81.
Steroids, vol. 29, (1977), No. 5, an article by Gapta et al, pp. 669–677.

Primary Examiner—Elbert L. Roberts
Attorney, Agent, or Firm—Bierman & Muserlian

[57] ABSTRACT

Novel radioactive steriods labelled with tritium of the formula

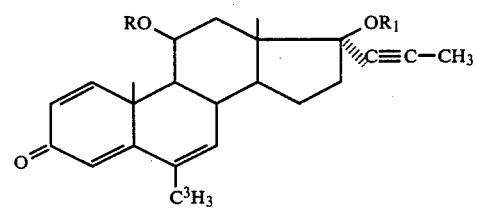

wherein $^3H$ is tritium and R and $R_1$ are individually selected from the group consisting of hydrogen, alkyl of 1 to 6 carbon atoms and acyl of an organic carboxylic acid of 1 to 10 carbon atoms useful for revealing receptors of glucocorticoids and in determining the number of fixation sites on glucocorticoids and novel intermediates.

8 Claims, No Drawings

NOVEL RADIOACTIVE STEROIDS

STATE OF THE ART

U.S. Pat. No. 4,233,297 describes the non-radioactive form of 6-methyl-17α-(prop-1-ynyl)-Δ$^{1,4,6}$-androstatriene-11β,17β-diol-3-one and French patents No. 2,398,076 and 2,398,077 describe different steroids marked with tritium.

OBJECTS OF THE INVENTION

It is an object of the invention to provide the novel radioactive steroids of formula I and a novel process and novel intermediates therefore.

It is another object of the invention to provide a novel method of revealing glucocorticoid receptors and determining the number of fixation sites of the glucocorticoids.

These and other objects and advantages of the invention will become obvious from the following detailed description.

THE INVENTION

The novel compounds of the invention are radioactive steroids labelled with tritium of the formula

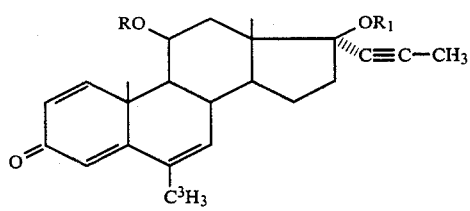

wherein $^3$H is tritium and R and R$_1$ are individually selected from the group consisting of hydrogen, alkyl of 1 to 6 carbon atoms and acyl of an organic carboxylic acid of 1 to 10 carbon atoms.

Examples of R and R$_1$ are hydrogen; alkyl such as methyl, ethyl, propyl, isopropyl, butyl, sec-butyl, tert-butyl, pentyl, iso-pentyl, sec-pentyl, tert-phenyl, neo-pentyl, hexyl, iso-hexyl, sec-hexyl and tert-hexyl; and acyl such as formyl, acetyl, propionyl, butyryl, isobutyryl, valeryl, caproyl, benzoyl, capryloyl, methoxy-carbonyl and ethoxy-carbonyl.

A preferred compound of the invention is 6-methyl-$^3$H$_3$-17α-(prop-1-ynyl)-Δ$^{1,4,6}$-androstatriene-11β,17β-diol-3-one.

The novel process of the invention for the preparation of the compounds of formula I comprises reacting a compound of the formula

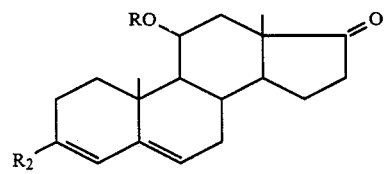

wherein R has the above definition and R$_2$ is alkoxy of 1 to 6 carbon atoms, acyloxy of 2 to 12 carbon atoms, or is the residue of a cyclic secondary amine with a halogen-methylation agent to obtain a product of the formula

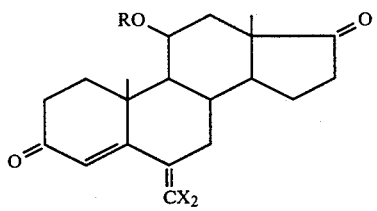

wherein X is halogen, reducing the latter with tritium in the presence of a catalyst to obtain a compound of the formula

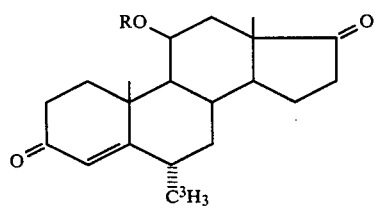

blocking the 3-keto group in an acid medium by reaction with an O-alkylation agent of the formula H—C—(OR$_3$)$_3$ wherein R$_3$ is alkyl of 1 to 6 carbon atoms to obtain a product of the formula

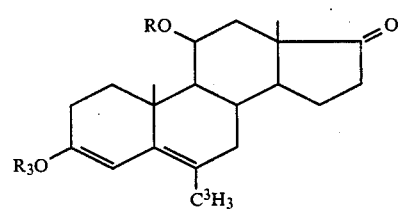

wherein R and R$_3$ have the above definitions, reacting the latter with a propynylating agent to obtain a compound of the formula

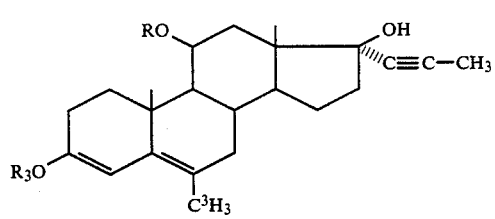

and reacting the latter with a dehydrogenating agent to obtain a product of formula I wherein R$_1$ is hydrogen, which if desired, the 17β-hydroxyl function may be etherified or esterified, and if R is hydrogen, one or other of the hydroxyl functions at 11β and 17β may be selectively etherified or esterified or the two hydroxyl functions at 11β and 17β are etherified or esterified.

Examples of R$_2$ are the residue of cyclic secondary amines such as for example, pyrrolidino, morpholino or piperidino.

In a preferred procedure of the process the halogen-methylation agent is carbon tetrabromide and the reaction is carried out under an inert atmosphere in dioxane in the presence of pyridine at ambient temperature and then at the reflux temperature of the mixture; the catalyst in the presence of which tritium is reacted is palladium hydroxide and the operation is carried out in dioxane in the presence of triethylamine. The O-alkylation agent of the 3-keto group of the product of formula IV is ethyl orthoformate and the operation is carried out under an inert atmosphere in an acid medium; the propynylating agent reacting with the product of formula V is propyn-1-yl magnesium bromide and the operation is carried out under an inert atmosphere in tetrahydrofuran; the dehydrogenating agent reacted with the product of formula VI is dichlorodicyanoquinone and the operation is carried out under an inert atmosphere in an aromatic or chlorinated solvent such as benzene or methylene chloride.

The etherification and/or esterification of the products of formula I can be effected by the usual methods. The etherification can, for example, be effected with an etherification agent such as an alkyl or aryl halide, or a dialkyl sulfate. The esterification can, for example, be effected with an esterification agent such as a functional derivative of an acid such as a chloride of an acid, or an anhydride.

The ways of carrying out the process of the invention can be still further illustrated by the fact that during the action of the halogen-methylation agent on a product of formula II, there are successively produced the condensation of the said agent on the steroid at ambient temperature, then, under the effect of the heat, the dehalohydration of the molecule formed in situ.

The invention also has as its object the use of the products of formula I, and particularly 6-methyl-$^3H_3$-17α-(prop-1-ynyl)-$\Delta^{1,4,6}$-androstatrien-11β,17β-diol-3-one in revealing the receptors of glucocorticoids and in determining the number of fixation sites of the glucocorticoids in the tissues of the organs of humans and animals.

The invention also has as its object the means for revealing the receptors of the glucocorticoids and the determining of the number of sites of fixation of the glucocorticoids, comprising a product such as is defined by the formula I and particularly 6-methyl-$^3H_3$-17α-(prop-1-ynyl)-$\Delta^{1,4,6}$-androstatrien-11β,17β-diol-3-one.

As new industrial intermediates are 6-dibromomethylen-$\Delta^4$-androstene-11β-ol-3,17-dione; 6-methyl-$^3H_3$-$\Delta^4$-androstene-11β-ol-3,17-dione; 3-ethoxy-6-methyl-$^3H_3$-$\Delta^{3,5}$-androstadiene-11β-ol-17-one and 3-ethoxy-6-methyl-$^3H_3$-17α-(prop-1-ynyl)-$\Delta^{3,5}$-androstadiene-11β,17β-diol.

The products of formula I, and particularly 6-methyl-$^3H_3$-17α-(prop-1-ynyl)-$\Delta^{1,4,6}$-androstatriene-11β,17β-diol-3-one, enable the receptors of glucocorticoids to be revealed and the number of sites of fixation of the glucocorticoids to be determined. It is known that non-radioactive 6-methyl-17α-(prop-1-ynyl)-$\Delta^{1,4,6}$-androstatriene-11β,17β-diol-3-one fixes selectively on the glucocorticoid receptors [TEUTSCH et al., STEOIDS, Vol. 38, No. 6, p. 651–665 (1981)]. Otherwise, other natural or synthetic corticoids which are used for this type of experiment, simultaneously fix on other steroid receptors and particularly on mineralocorticoid receptors. However, during such experiments with non-radioactive 6-methyl-17α-(prop-1-ynyl)-$\Delta^{1,4,6}$-androstatriene-11β,17β-diol-3-one, particularly when the tissues of oxygen examined included simultaneously glucocorticoid and mineralocorticoid receptors, it was often necessary to adopt a succession of long and complicated methods.

It has now been established that radioactive products of formula I, and particularly 6-methyl-$^3H_3$-17α-(prop-1-ynyl)-$\Delta^{1,4,6}$-androstatriene-11β,17β-diol-3-one, offer the same selective reactivity in respect of the glucocorticoid receptors as the similar non-radioactive products. Because of the radioactivity of the products of formula I, it is much easier to reveal the existence of the glucocorticoid receptors in the tissues of organs when mineralocorticoid receptors are also present, thanks to the use of the usual methods of liaison measurements taking advantage of radioactive products. In addition, what was not possible with a non-radioactive product, such, for example, as determining of the number of sites of fixation of the glucocorticoid receptors, becomes realizable by the use of the products of formula I.

It can also be seen that when products of formula I, and particularly 6-methyl-$^3H_3$-17α-(prop-1-ynyl)-$\Delta^{1,4,6}$-androstatriene-11β,17β-diol-3-one, are used in vivo because of their radioactivity, one could easily determine the exact emplacement of the sites of fixation of the glucocorticoids. The products of formula I can thus be used as a particularly interesting means of revealing the glucocorticoid receptors and of determining the number of fixation sites, for example in tissues of organs including glucocorticoid and mineralocorticoid receptors such as the hippocampus and other structures of the brain, the kidneys, the colon, the hypophysis and other peripheral tissues.

The products of formula I in the conditions of working in vitro and in certain tissues are not subject to metabolism in the incubation conditions in which corticosterone or cortisol, for example, are metabolized in certain tissues. The techniques utilized for revealing the steroid receptors and determining of the number of fixation sites are those most currently used in this domain such as RAYNAUD et al., J. of STEROID BIOCHEM., Vol. 6 (1975) pages 615–622 and MOGUILEWSKY et al., J. of STEROID BIOCHEM., Vol. 12, (1980), pages 309–314.

During experiments with 6-methyl-$^3H_3$-17α-(prop-1-ynyl)-$\Delta^{1,4,6}$-androstatriene-11β,17β-diol-3-one (product A), it was found that it easily satisfied all the requirements necessary for revealing the glucocorticoid receptors and determining the fixation sites. It was also established that (a) Product A does not give rise to any specific fixation on the plasmatic proteins in animals or humans, which proteins generally contaminate any preparation of tissue receptors. (b) At 0° C., the constant of association of Product A, ($K_a \simeq 10^9 M^{-1}$) with the glucocorticoid receptors of cytosol of rat thymus, supplied by reading of adsorption by means of carbon-dextrane, is about twice as high as that of dexamethazone; (c) Product A is endowed with a high speed of association ($K_{+1} \simeq 10^6 M^{-1} mn^{-1}$) and with a low speed of dissociation towards the glucocorticoid receptors in the thymus ($t\frac{1}{2} \simeq 16$ hrs) and towards the glucocorticoid receptors of the hippocampus ($t\frac{1}{2} \simeq 24$ hrs). In these two tissues, it is dissociated according to a curve with one slope, while $^3H$-dexamethasone and $^3H$-corticosterone in the hippocampus cytosol present a dissociation curve with two slopes which is characteristic of a fixation on at least two liaison sites of glucocorticoids and mineralocorticoids. (d) At 0° C. and 15° C., product A forms complexes with thymus glucocorticoid receptors which are stable for at least 24 hours. In these conditions, the said product A does not show any loss of tritium and is not subject to metabolism and only shows a weak non-specific fixation. (e) When submitted to incubation at 15° C. for 24 hours, product A totally replaces non-radioactive corticosterone and non-radioactive cortisol fixed on glucocorticoid receptors. For this reason, it permits the total number of glucocorticoid fixation sites to be determined in different physiological conditions.

In the following examples there are described several preferred embodiments to illustrate the invention. However, it is to be understood that the invention is not intended to be limited to the specific embodiments.

EXAMPLE 1

6-methyl-$^3H_3$-17α-(prop-1-ynyl)-$\Delta^{1,4,6}$-androstatriene-11β,17β-diol-3-one

STEP A:

6-dibromomethylene-$\Delta^4$-androstene-11β-3,17-dione

A mixture of 3.7 g of 3-ethoxy-$\Delta^{3,5}$-androstadiene-11β-ol-17-one (described at Japanese patent application Serial No. 9577/71), 20 ml of dioxane, 1 ml of pyridine and 4 g of carbon tetrabromide was stirred at ambient temperature for about 24 hours under an inert atmosphere and was then filtered. The precipitate was washed several times with dioxane and the combined organic filtrates were heated at reflux for about 4 hours. After the solution was cooled, 50 ml of 2N hydrochloric acid were added with stirring over about ten minutes and after extraction with ethyl acetate, the organic phases were washed successively with water and with water saturated with sodium chloride, then dried and evaporated to dryness. The residue was taken up in ethyl acetate and crystallization was effected at −20° C. The product was crystallized from ethyl acetate to obtain 0.6 g of 6-dibromomethylene-$\Delta^4$-androstene-11β-ol-3,17-dione melting at 256° C.

UV Spectrum (EtOH): max. at 252 nm; inflexion at 284 nm.

The purity was improved by thin layer chromatography on silica and elution with a 1—1 mixture of cyclohexane and ethyl acetate (Rf=0.2).

STEP B:

6-methyl-$^3H_3$-$\Delta^4$-androstene-11β-ol-3,17-dione

A mixture of 80 mg of the dibrominated product of Step A, 2 ml of dioxane, 20 mg of 2% palladized carbon on talc and 120 μl of triethylamine was cooled by liquid nitrogen and under vacuum, 15.5 ml of tritium with a specific activity of 58 Ci/mmol was added thereto and the mixture was allowed to return to ambient temperature. It is then added towards 40° C., and stirred under tritium until absorption was complete. After recovering excess tritium, the mixture was filtered and 1 ml of 2N HCl was added thereto. The mixture stood at rest for about 1 hour at ambient temperature and was extracted with ethyl acetate. The organic phase was washed with water, dried and evaporated to dryness to obtain 60 mg of crude 6-methyl-$^3H_3$-$\Delta^4$-androstene-11β-ol-3,17-dione which was utilized as is for the next step.

UV Spectrum (EtOH) max. at 240 nm.

The purity of the product was improved by thin layer chromatography over silica and elution with a 1—1 mixture of cyclohexane and ethyl acetate (Rf=0.17).

STEP C:

3-ethoxy-6-methyl-$^3H_3$-$\Delta^{3,5}$-androstadiene-11β-ol-17-one

Under an inert atmosphere and with stirring, the tritiated product of Step B was introduced into 120 μl of ethyl orthoformate and 20 μl of ethyl orthoformate with 1% of acetyl chloride, and then 400 μl of ethanol were added thereto. Stirring was maintained at ambient temperature for about 10 minutes and then 100 μl of triethylamine were added. The mixture was evaporated to dryness under reduced pressure to obtain 58 mg of crude 3-ethoxy-6-methyl-$^3H_3$-$\Delta^{3,5}$-androstadiene-11β-ol-17-one which was used as is for the next step.

The purity of the product was improved by thin layer chromatography on silica and elution with a 1—1 mixture of cyclohexane and ethyl acetate. (Rf=0.5).

STEP D:

3-ethoxy-6-methyl-$^3H_3$-17α-(prop-1-ynyl)-$\Delta^{3,5}$-androstadiene-11β,17β-diol Under an inert atmosphere and with stirring, the product of Step C was introduced into 100 μl of tetrahydrofuran and 2 ml of 1M solution of propy-1-ynyl magnesium bromide in tetrahydrofuran were added thereto. The mixture was maintained under stirring at ambient temperature for about half an hour and 5 ml of a 10% aqueous solution of ammonium chloride were then added. The mixture was extracted with ethyl acetate and the extract was washed with water, dried and evaporated to dryness to obtain 60 mg of 3-ethoxy-6-methyl-$^3H_3$-17α-(prop-1-ynyl)-$\Delta^{3,5}$-androstadiene-11β,17β-diol with an activity of 7 Ci which was used as is for the next step.

The purity of the product was improved by thin layer chromatography on silica and elution with a 1—1 mixture of cyclohexane and ethyl acetate. (Rf=0.40).

STEP E:

6-methyl-$^3H_3$-17α-(prop-1-ynyl)-$\Delta^{1,4,6}$-androstatriene-11β,17β-diol-3-one Over a period of 15 minutes with stirring and under an inert atmosphere, a solution of 90 mg of dichlorodicyanoquinone was added to the product of Step D in 0.5 ml of benzene and stirring was maintained for about half an hour. Then, 0.5 ml of acetone, 100 μl of sodium bisulfite (an aqueous solution of d=1.32), and 1 ml of a 10% aqueous solution of sodium bicarbonate were added and after extraction with ethyl acetate the extract was washed with a 10% aqueous solution of sodium bicarbonate. After purification by high pressure liquid chromatography on silica and elution with a 99-1 chloroform-methanol mixture with 5% of water, 50.3 mg of 6-methyl-$^3H_3$-17α-(prop-1-ynyl)-$\Delta^{1,4,6}$-androstatriene-11β,17β-diol-3-one were obtained with a specific activity is 37 Ci/mmol.

Thin layer chromatograhy on silica and elution with a 1—1 mixture of cyclohexane and ethyl acetate, yielded a product with an Rf=0.15.

Various modifications of the products and method of the invention may be made without departing from the spirit or scope thereof and it should be understood that the invention is intended to be limited only as defined in the appended claims.

What we claim is:

1. A process for the preparation of a compound of the formula wherein ³H is Tritium and R and R₁ are individually selected from the group consisting of hydrogen, alkyl of 1 to 6 carbon atoms and acyl of an organic carboxylic acid of 1 to 10 carbon atoms comprising reacting a compound of the formula

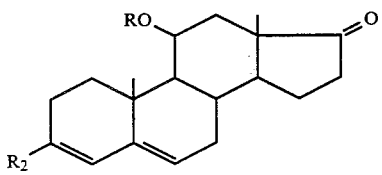

wherein R has the above definition and R₂ is alkoxy of 1 to 6 carbon atoms, acyloxy of 2 to 12 carbon atoms, or is the residue of a cyclic secondary amine with a halogen-methylation agent to obtain a product of the formula

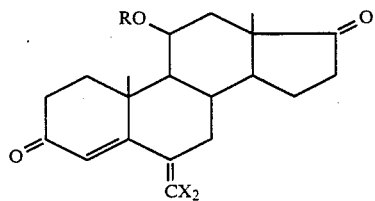

wherein X is halogen, reducing the latter with tritium in the presence of a catalyst to obtain a compound of the formula

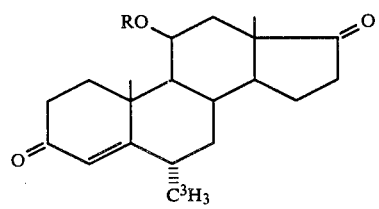

blocking the 3-keto group in an acid medium by reaction with an O-alkylation agent of the formula H-C(OR₃)₃ wherein R₃ is alkyl of 1 to 6 carbon atoms to obtain a product of the formula

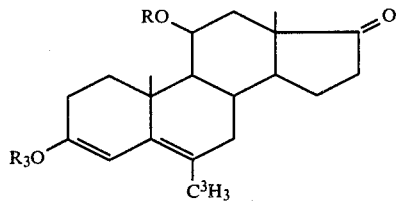

wherein R and R₃ have the above definitions reacting the latter with a propynylating agent to obtain a compound of the formula

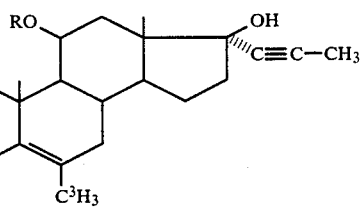

and reacting the latter with a dehydrogenating agent to obtain a product of formula I wherein R₁ is hydrogen, which if desired, the 17β-hydroxyl function may be etherified or esterified, and if R is hydrogen, one or other of the hydroxyl functions at 11β and 17β may be selectively etherified or esterified or the two hydroxyl functions at 11β and 17β are etherified or esterified.

2. The process of claim 1 wherein the halogen-methylation agent is carbon tetrabromide and the operation is carried out under inert atmosphere in dioxane in the presence of pyridine at ambient temperature and then at the reflux temperature of the mixture.

3. The process of claim 1 wherein the catalyst in the presence of which tritium is acted is palladium hydroxide and the operation is carried out in dioxane in the presence of triethylamine.

4. The process of claim 1 wherein the O-alkylating ag of the 3-ketone group of formula IV is ethyl orthoformate and the operation is carried out under an inert atmosphere in an acid medium.

5. The process of claim 1 wherein the propynylating agent which is reacted with the product of formula V is propyn-1-yl magnesium bromide and the operation is carried out under an inert atmosphere in tetrahydrofuran.

6. The process of claim 1 wherein the dehydrogenating agent which is reacted with the product of formula VI is dichlorodicyanoquinone and the operation is carried out under an inert atmosphere in an aromatic or chlorinated solvent.

7. In a method of revealing glucocorticoid receptors and determing the number of fixation sites of glucocorticoids, the improvement comprising using a compound of the formula

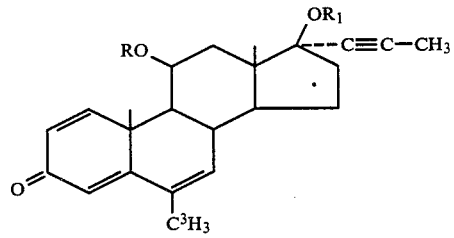

wherein ³H is Tritium and R and R₁ are individually selected from the group consisting of hydrogen, alkyl of 1 to 6 carbon atoms and acyl of an organic carboxylic acid of 1 to 10 carbon atoms.

8. The method of claim 7 wherein the active compound is 6-methyl-³H₃-17α-(prop-1-ynyl)-Δ$^{1,4,6}$-androstatriene-11β,17β-diol-3-one.

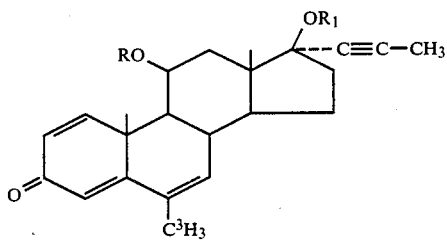

* * * * *